United States Patent [19]

Cheney et al.

[11] 4,450,724

[45] May 29, 1984

[54] METHOD FOR DETERMINING THE SIZE OF METAL CARBIDE GRAINS IN CEMENTED CARBIDES

[76] Inventors: Richard F. Cheney, 50 Hemlock Rd.; Anil Bansal, 26 Larch Rd.; Edward R. Kimmel, 153 Center St., all of Sayre, Pa. 18840

[21] Appl. No.: 434,437

[22] Filed: Oct. 14, 1982

[51] Int. Cl.³ .................... G01N 15/00; G01N 27/72
[52] U.S. Cl. .......................... 73/432 R; 73/432 PS; 324/326

[58] Field of Search .......... 73/432 PS, 432 Z, 432 R; 324/201, 326

[56] References Cited

U.S. PATENT DOCUMENTS 1,596,615  8/1926  Malmberg et al. ................ 324/226

Primary Examiner—James J. Gill

[57] ABSTRACT

In a method for determining the grain size of a cemented carbide for a given quantity and composition of the metal binder, the grain size is determined as a function of the coercive force and quantity of metal binder.

6 Claims, 3 Drawing Figures

METHOD FOR DETERMINING THE SIZE OF METAL CARBIDE GRAINS IN CEMENTED CARBIDES

Copending application is entitled Method of Recovering Metal Carbides application Ser. No. 434,987.

BACKGROUND OF THE INVENTION

The present invention relates to a method for determining the size of metal carbide grains in cemented metal carbides.

The grain size of metal carbide grains present in cemented carbides is typically measured by a complex and time consuming procedure where a flat surface of the cemented carbide to be examined is polished and chemically etched. The etching permits the grains to be distinguished from the areas of matrix material when a micrograph of the surface is prepared. There are several tedious methods which involve the counting of the carbide grains to determining grain size.

SUMMARY OF INVENTION

The above discussed methods of determining grain size are time consuming and require the destruction of the cemented metal carbide. It is desirable to develop a method for determining the grain size which is non-destructive and can be rapidly implemented.

In accordance with the present invention, there is provided a method of determining the size of grains of refractory metal carbide in a cemented metal carbide comprising determining the composition of the metal binder material, determining the coercive force of the cemented metal carbide, obtaining a determination of metal carbide grain size based on coercive force being a function of grain size for a determined composition of metal binder.

The present invention provides for a rapid determination of the relative grain size without destruction of the cemented metal carbide.

DETAILED DESCRIPTION

Cemented metal carbides comprise one or more transitional carbides of Groups IVB, VB and VIIB of the Periodic Table which are cemented or bonded by one or more matrix metals selected from the group consisting of iron, nickel and cobalt. Typical cemented carbides may contain tungsten carbide in a cobalt matrix, titanium carbide in a cobalt matrix or titanium carbide in a nickel matrix. Other intentional additives may be used, such as molybdenum may be used with nickel to wet the carbide phase.

The starting powders used in the cemented carbide compositions are generally in pure form. It is desirable to exclude impurities such as oxygen which tends to have deleterious effects on the density of the composition. On the other hand, minor amounts of many impurities may be present such as small amounts of other metals such as titanium, zirconium, tantalum, or niobium. To have a metal carbide suitable for the non-destructive method of determining grain size in accordance with the method of the present invention, it is preferable that the unknown additives or impurities be less than about 2% by weight.

The contents and quantity of various elements in the cemented metal carbide are measured. This may be performed by any method known in the art, but is preferably performed by a non-destructive method that can be performed rapidly such as x-ray fluorescence (XRF) or emission spectrometry. According to these techniques, elements contained in the samples are excited by x-rays or high-intensity spark. For the XRF technique, the characteristic x-rays given off are analyzed. The spectrum of x-rays and their energy levels are analyzed to provide a quantitative analysis of the sample composition. For the emission spectrometry, the resultant light is dispersed by a diffraction grating. The spectrum line intensities at specific wavelengths are proportional to the concentration of the individual elements in the sample.

The coercive force of the sample is next determined. Typically the coercive force may be determined by placing a sample into a magnetizing and measuring coil magnetized to saturation to provide a magnetic field which is detected by field sensors. Then an increasing opposing field is created until the field produced by the sample reaches zero. At this instant, the induction is zero and the field in the coil is the coercive force (Hc) of the sample.

Figure 1:
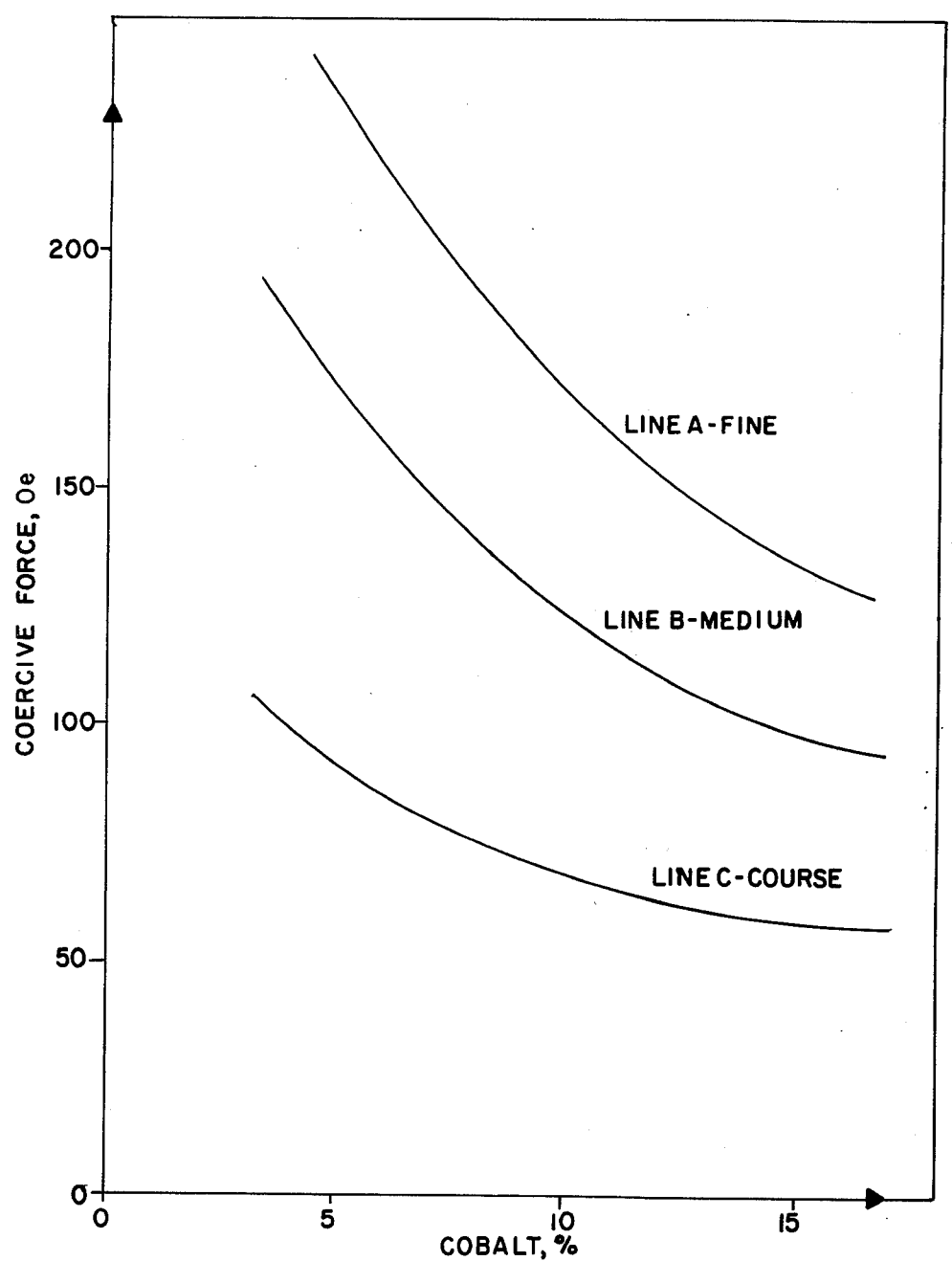
FIG. 1 is a plot of coercive force vs. percent metal binder for three representative grain sizes.
Figure 2:
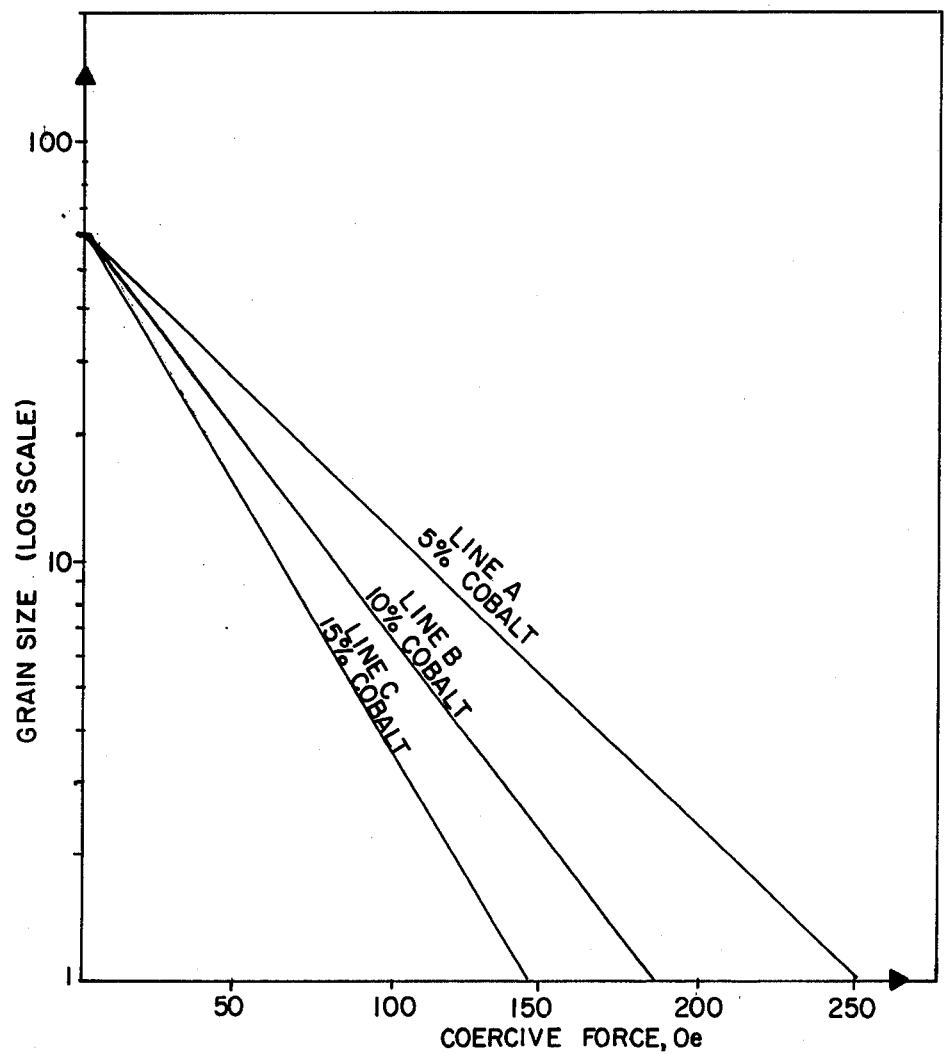
FIG. 2 is a plot of grain size vs. coercive force.

According to the principles of the present invention, a determination of metal carbide grain size is based on coercive force being a function of grain size for a determined composition of metal carbide grains and binder metal. FIG. 1 is a graph plotting coercive force against the percent metal binder for three grain sizes. The grain size represented as line A is fine, line B is medium, and line C is coarse. In FIG. 2, the log of grain size is plotted against coercive force to obtain a series of three lines with a common intercept. On the Cartesian graph, the log of grain size (log G) is the ordinate and coercive force (Hc) is the abscissa. Line A represents a constant low weight percent metal binder content, line B a medium binder content and line C a high metal binder content. The graph has the following mathematical formula:

$$\log G = -m \times Hc + I_1 \quad (1)$$

m = Positive slope
Hc = Coercive force in oersteds
$I_1$ = Intercept on Y-axis
G = Grain size in microns (μm).

Figure 3:
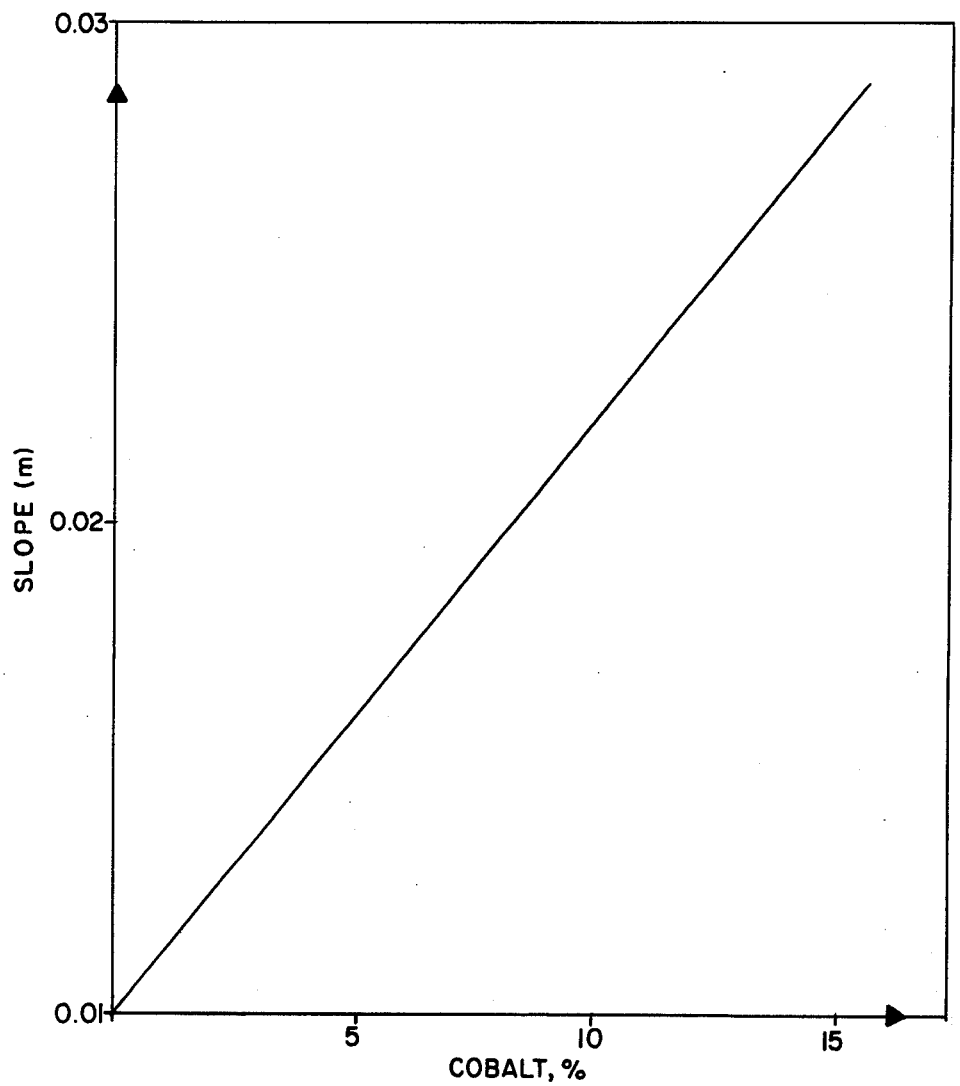
FIG. 3 is a plotting of numerical value of slopes from FIG. 2 vs. metal binder content.

Since the slope m of the above equation appears to be a function of metal binder content, the slope m was plotted against the metal binder content in FIG. 3. A single straight line was obtained having the formula $$m = MB + I_2 \quad (2)$$

m = slope from FIG. 2
M = slope of FIG. 3
B = percent binder in cemented metal carbide
$I_2$ = Intercept on Y-axis By substituting for m in Equation 1 the following equation is obtained.

$$\log G = -(MB + I_2)Hc + I_1 \quad (3)$$

Cemented carbides may have a similar composition only in terms of metal binder content or only in terms of metal carbide content. If both carbide and binder are compositionally similar, the entire cemented carbide is considered compositionally similar. Similarity in terms of composition as set forth herein is intended to refer to similarity in terms of quality and not quantity. Similar compositions are preferably substantially identical in identified materials but may have different quantities of those materials as expressed in weight percent.

EXAMPLE 1

The following three grades of virgin starting tungsten carbide power were chosen. Each lot of starting powder has a different particle size as determined by FSSS measurement, three are indicated. Each grade produces a different grain size when made into a cemented carbide. The cemented carbide grain size is proportional to the FSSS number for virgin powder. The virgin powder is typically made directly by the carburization of tungsten powder and is not tungsten carbide directly reclaimed from scrap. Each FSSS number corresponds to a grade designation.

| Cemented Carbide Grain Size | Starting FSSS No. | WC GRADE |
|---|---|---|
| Fine | 1.33 | SC11 |
| Medium | 3.70 | SC40 |
| Coarse | 13.00 | SC65 |

Grade powders were made in a four inch attritor mill. Three different levels of virgin cobalt, namely 5%, 10% and 15% were used to make a total of nine lots. For each lot, carbide powder, cobalt and 2% wax were milled for one hour at 150 rpm each to form respective lots of grade powder. About 200 grams of each of the nine lots of grade powder were milled in hexane with 2000 grams of tungsten carbide balls. The nine resulting lots were pressed into standard use bars and thumbnails. All of the pieces were dewaxed and sintered at 1435° C. in hydrogen. Table 1 shows the test results:

TABLE I

| | | | Coercive Force, Oe | | |
|---|---|---|---|---|---|
| Sample | % Co | WC | Bar | Thumbnail | Average |
| 1 | 5 | SC117 | 233 | 233 | 233 |
| 2 | 10 | SC117 | 171 | 173 | 172 |
| 3 | 15 | SC117 | 132 | 134 | 133 |
| 4 | 5 | SC140 | 173 | 173 | 173 |
| 5 | 10 | SC140 | 126 | 124 | 125 |
| 6 | 15 | SC140 | 97 | 98 | 98 |
| 7 | 5 | SC65 | 92 | 92 | 92 |
| 8 | 10 | SC65 | 69 | 69 | 69 |
| 9 | 15 | SC65 | 58 | 58 | 58 |

By visual examination of the microstructures of the cemented carbides the grain sizes for respective samples 1-3 were identical. The grain sizes for respective samples 4-6 were identical, and the grain sizes for samples 7-9 were identical. This is due at least partially to the processing of the virgin tungsten carbide powder under conditions where the final grain size is directly proportional to the size of the starting powder in Fisher Sub Sieve Size. The difference in coercieve force is attributable to the cobalt content since all samples are compositionally the same. The generated data of Table 1 can be graphically presented so as to correspond to the graph of FIG. 1. The following equation is thus correct for the above generated data.

$$\text{Log } G = -(MB + I_2)Hc + I_1$$

Since log GRAIN SIZE <=> log FSSS $$\text{Log } FSSS = -(MB + I_2)Hc + I_1 \tag{3a}$$

FSSS = Fisher Sub Sieve Size of the starting virgin powder.

The following equation based on equation 3a holds true for the above data.

$$Hc = \frac{4078 - 1000 (\log FSSS)}{1.21 \times \% Co + 10} \tag{4}$$

%Co = Percent cobalt in the cemented carbide.

EXAMPLE 2

Equation 4 was tested by randomly selecting samples 1–11 of Table II, determining the composition and measuring the coercive force of each sample, calculating the coercive force from known properties of samples, and then comparing the calculated value with the measured value. As set forth in table II, the calculated and measured values compare favorably within the limits of experimental error. The composition of the sample was measured by x-ray fluorescence using an EG&G Ortec (Tefa-III) machine. The coercive force was measured on a Forester Coercive Force Instrument. Since coercive force from known properties corresponds closely with coercive force as measured, the above equation 4 is verified. Hence, the equation may also be used to determine grain size as a function of coercive force according to the following equation.

$$\text{Log } G = I_1 - Hc[(M)(\%Co) + I_2] \tag{5}$$

The FSSS of virgin metal carbide powder initially used for making the cemented carbide may be determined since the cemented carbide grain size is proportional to the FSSS.

TABLE II

| Sample | Carbide Composition | Measured Hc | Calculated H |
|---|---|---|---|
| 1 | WC | 125 | 125 |
| 2 | WC | 98 | 98 |
| 3 | WC | 92 | 94 |
| 4 | WC | 69 | 68 |
| 5 | WC | 58 | 54 |
| 6 | WC | 157 | 176 |
| 7 | WC | 84 | 96 |
| 8 | WC | 162 | 168 |
| 9 | WC + .5TaC | 119 | 122 |
| 10 | WC + 10TaC + 5TiC | 164 | 176 |
| 11 | WC + TaC + 5TiC | 75 | 72 |

INDUSTRIAL APPLICABILITY

The process of the present invention is particularly useful for determining the grain size of cemented metal carbides. The grain size is an important factor is determining the use properties of a cemented metal carbide.

We claim:

1. A method of determining the size of grains of refractory metal carbide in a cemented metal carbide comprising determining the composition and quantity of the metal binder material, determining the coercive force of the cemented metal carbide, obtaining a determination of metal carbide grain size based on coercive force being a function of grain size for said determined composition of metal binder and said determined quantity of metal binder.

2. A method according to claim 1 wherein the grain size is a function of coercive force for a determined composition according to an approximate straight line when plotted on a Cartesian graph with the log G as the ordinate and Hc is the abscissa, where G is grain size and Hc is coercive force in oersteds according to the following equation:

$$\log G = I_1 - mHc$$

m = slope of said straight line
$I_1$ = intercept of straight line with ordinate.

3. A method according to claim 3 wherein the grain size is the average grain size.

4. A method according to claim 4 wherein at least a major portion of the binder consists essentially of cobalt.

5. A method according to claim 2 wherein a major portion of said metal carbide consists essentially of grains of tungsten carbide.

6. A method according to claim 2 wherein G is proportional to the FSSS of the starting metal carbide powder of the cemented metal carbide.

* * * * *